United States Patent
Kasumi et al.

(10) Patent No.: US 9,584,795 B2
(45) Date of Patent: Feb. 28, 2017

(54) WIRELESS TRANSFER SYSTEM

(71) Applicant: OLYMPUS CORPORATION, Hachioji-shi, Tokyo (JP)

(72) Inventors: Makoto Kasumi, Hachioji (JP); Hideki Tashiro, Hino (JP); Junichi Tashiro, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/153,006

(22) Filed: May 12, 2016

(65) Prior Publication Data
US 2016/0261846 A1 Sep. 8, 2016

Related U.S. Application Data

(63) Continuation of application No. PCT/JP2014/077788, filed on Oct. 20, 2014.

(30) Foreign Application Priority Data

Dec. 4, 2013 (JP) ................................ 2013-251238

(51) Int. Cl.
*H04N 13/00* (2006.01)
*H04N 7/18* (2006.01)
(Continued)

(52) U.S. Cl.
CPC ....... *H04N 13/0059* (2013.01); *A61B 1/0005* (2013.01); *A61B 1/00006* (2013.01);
(Continued)

(58) Field of Classification Search
CPC ................................................ H04N 13/0059
See application file for complete search history.

(56) References Cited

U.S. PATENT DOCUMENTS

2007/0263937 A1 11/2007 Rizko
2008/0139881 A1* 6/2008 Cover ................ A61B 1/00016
600/103
(Continued)

FOREIGN PATENT DOCUMENTS

EP 1 889 564 A1 2/2008
JP H0998985 A 4/1997
(Continued)

OTHER PUBLICATIONS

Oct. 20, 2015 Office Action issued in Japanese Patent Application No. 2015-535638.
(Continued)

*Primary Examiner* — Tung Vo
*Assistant Examiner* — Rowina Cattungal
(74) *Attorney, Agent, or Firm* — Oliff PLC

(57) ABSTRACT

A wireless transfer system includes: a wireless transmission section including: an input section configured to receive, as an input signal, one of a first video signal provided with ancillary information including identification information of a high-definition 3D/2D video signal and a second video signal not including the identification information; a video signal extraction section configured to extract one of the high-definition video signal and the second video signal from the input signal; an ancillary information extraction section configured to extract the ancillary information; a wireless video transmitter configured to wirelessly transmit extracted one of the high-definition video signal and the second video signal; and the like; and a wireless reception section including: a wireless video receiver configured to receive wirelessly transmitted one of the high-definition video signal and the second video signal; a wireless ancillary information receiver configured to receive the wirelessly transmitted ancillary information; and the like.

13 Claims, 12 Drawing Sheets

(51) Int. Cl.
*A61B 1/00* (2006.01)
*A61B 1/05* (2006.01)
*A61B 1/04* (2006.01)
*H04N 5/225* (2006.01)
*H04N 13/02* (2006.01)
*H04N 13/04* (2006.01)

(52) U.S. Cl.
CPC ...... *A61B 1/00009* (2013.01); *A61B 1/00016* (2013.01); *A61B 1/00018* (2013.01); *A61B 1/00048* (2013.01); *A61B 1/00193* (2013.01); *A61B 1/04* (2013.01); *A61B 1/05* (2013.01); *H04N 5/225* (2013.01); *H04N 7/18* (2013.01); *H04N 7/183* (2013.01); *H04N 13/0066* (2013.01); *H04N 13/026* (2013.01); *H04N 13/0452* (2013.01); *H04N 2005/2255* (2013.01)

(56) References Cited

U.S. PATENT DOCUMENTS

| | | |
|---|---|---|
| 2008/0170834 A1 | 7/2008 | Shibata |
| 2009/0027490 A1 | 1/2009 | Hirai et al. |
| 2009/0322948 A1 | 12/2009 | Funabiki et al. |
| 2010/0118120 A1 | 5/2010 | Takahashi et al. |
| 2010/0238270 A1* | 9/2010 | Bjelkhagen ........ H04N 13/0402 348/45 |

FOREIGN PATENT DOCUMENTS

| | | |
|---|---|---|
| JP | 2006334323 A | 12/2006 |
| JP | 2007306539 A | 11/2007 |
| JP | 2008035517 A | 2/2008 |
| JP | 2008072236 A | 3/2008 |
| JP | 2010114861 A | 5/2010 |
| JP | 2011197057 A | 10/2011 |
| JP | 2012110068 A | 6/2012 |
| JP | 2013094593 A | 5/2013 |
| WO | 2006/132154 A1 | 12/2006 |
| WO | 2007/094347 A1 | 8/2007 |
| WO | 2007/142785 A2 | 12/2007 |

OTHER PUBLICATIONS

Jan. 13, 2015 International Search Report issued in International Patent Application No. PCT/JP2014/077788.

Mar. 15, 2016 Decision to Grant issued in Japanese Patent Application No. 2015-535638.

* cited by examiner

WIRELESS TRANSFER SYSTEM

CROSS REFERENCE TO RELATED APPLICATION

This application is a continuation application of PCT/JP2014/077788 filed on Oct. 20, 2014 and claims benefit of Japanese Application No. 2013-251238 filed in Japan on Dec. 4, 2013, the entire contents of which are incorporated herein by this reference.

BACKGROUND OF THE INVENTION

1. Field of the Invention

The present invention relates to a wireless transfer system configured to wirelessly transfer a video signal of a high-definition three-dimensional image and the like.

2. Description of the Related Art

In recent years, endoscopes have been widely used in a medical field and the like. A stereoscopic endoscope system using a stereoscopic endoscope capable of three-dimensional view is widespread for a surgery under observation with an endoscope.

In endoscope systems including the case of the stereoscopic endoscope system, a position (standing position) where an operator stands around a bed with a patient generally changes in some cases according to progress of the surgery, and two monitors are arranged according to the change in the standing position of the operator.

In general, it is rare for the operator to perform three-dimensional observation all the time from start to end of the surgery. In a general surgery, the operator performs normal observation (2D observation) that is not for three-dimensional view and performs three-dimensional observation (3D observation) when a highly accurate treatment is necessary. Therefore, it is desirable to be able to handle switching of the 2D observation and the 3D observation during the surgery. In recent years, execution of high-definition 3D observation along with high-definition 2D observation is desired due to an increased number of pixels in an image pickup device.

Under the circumstances, in a stereoscopic endoscope system including two monitors, one three-dimensional monitor (will be called a 3D monitor) for three-dimensional observation (for 3D observation) needs to be mounted on a trolley provided with medical devices necessary in the stereoscopic endoscope system, and the other 3D monitor needs to be arranged separately from the trolley, at a position corresponding to the standing position of the operator.

In this case, a video signal outputted from a 3D mixer as a medical device mounted on the same trolley can be transferred to the 3D monitor mounted on the trolley through a cable. However, there is a drawback for the other 3D monitor, such as a long cable needs to be installed along a floor surface, and convenience is higher when the video signal is transferred wirelessly.

Japanese Patent Application Laid-Open Publication No. 2013-94593 as a first conventional example discloses an endoscope system configured to wirelessly transfer a video signal.

Japanese Patent Application Laid-Open Publication No. 2012-110068 as a second conventional example discloses a wireless transfer apparatus configured to transmit and receive a video signal provided with identification information for distinguishing high-definition (HD) 2D video and 3D video.

SUMMARY OF THE INVENTION

An aspect of the present invention provides a wireless transfer system including: a wireless transmission section including: an input section configured to receive one of a first video signal and a second video signal as an input signal, the first video signal being compliant with a first signal transfer standard provided with, at a head part of a high-definition video signal, ancillary information including at least identification information indicating one of a high-definition 3D video signal and a high-definition 2D video signal, the second video signal having a signal transfer rate lower than the first video signal and being compliant with a second signal transfer standard not including the identification information; a video signal extraction section configured to extract one of the high-definition video signal and the second video signal from the input signal; an ancillary information extraction section configured to extract the ancillary information including at least the identification information from the input signal; a wireless video transmitter configured to wirelessly transmit one of the high-definition video signal and the second video signal extracted by the video signal extraction section; a wireless ancillary information transmitter configured to wirelessly transmit the ancillary information extracted by the ancillary information extraction section, separately from one of the high-definition video signal and the second video signal wirelessly transmitted by the wireless video transmitter; and a control section configured to control operation of the wireless ancillary information transmitter according to an extraction result of the ancillary information; and a wireless reception section including: a wireless video receiver configured to receive one of the high-definition video signal and the second video signal wirelessly transmitted from the wireless video transmitter; a wireless ancillary information receiver configured to receive the ancillary information wirelessly transmitted from the wireless ancillary information transmitter; and an output signal control section configured to add the ancillary information to the high-definition video signal and output the high-definition video signal when the ancillary information is received and configured to output the second video signal when the ancillary information is not received, according to a reception result of the wireless video receiver and a reception result of the wireless ancillary information receiver.

DETAILED DESCRIPTION OF THE PREFERRED EMBODIMENTS

Hereinafter, an embodiment of the present invention will be described with reference to the drawings.

First Embodiment

Figure 1:
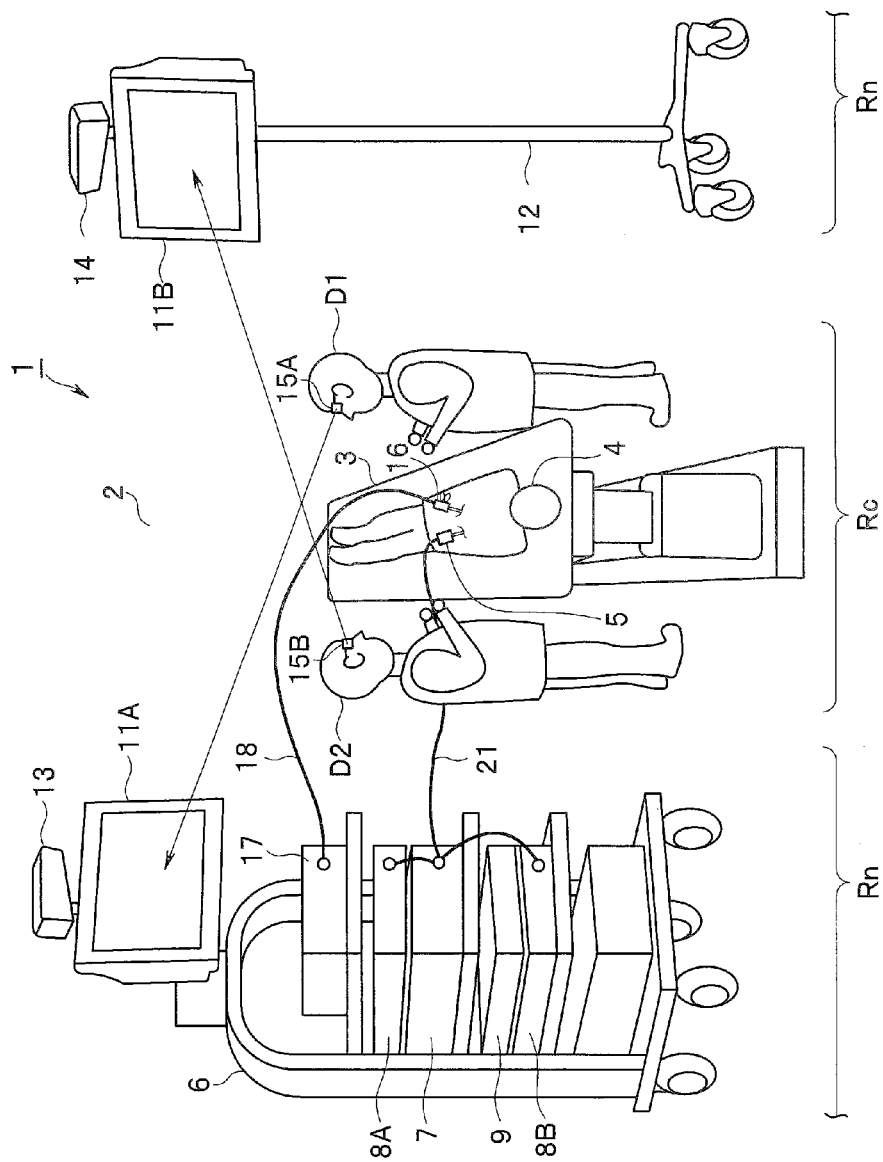
FIG. 1 is a diagram showing an entire configuration of a stereoscopic endoscope system including a wireless transfer system of the present invention.

As shown in FIG. 1, a stereoscopic endoscope system 1 including a wireless transfer system of the present invention includes: a stereoscopic endoscope (will also be called 3D endoscope) 5 inserted into, for example, an abdominal part of a patient 4 lying in a bed 3 in an operating room 2; a movable trolley 6 provided with a plurality of medical devices; and a light source apparatus 7 mounted on the trolley 6 and configured to supply illumination light to the 3D endoscope 5.

The stereoscopic endoscope system 1 further includes: first and second processors 8A and 8B as signal processing apparatuses configured to execute signal processing for two image pickup sections mounted on the 3D endoscope 5; and a 3D mixer 9 configured to generate a high-definition 3D video signal from left and right video signals generated by the first and second processors 8A and 8B.

Note that in the present embodiment, as described later, first image pickup sections 27A and 27B (see FIG. 2) forming the two image pickup sections are constituted by using high-pixel image pickup devices, and the first and second processors 8A and 8B generate respective high-definition (HD) 2D video signals (HD-SDI signals) from image pickup signals inputted from the first image pickup sections 27A and 27B, respectively, and output the signals to the 3D mixer 9.

The 3D mixer 9 applies double-speed processing based on HD 2D video signals to generate a high-definition 3D video signal that is a 3G-SDI signal compliant with a standard of a signal transfer rate of 3 Gbits/second (3 Gb/S) (or 3G-SDI standard). Note that the signal transfer rate of the HD-SDI signal as an HD video signal is ½ of that of the 3G-SDI signal. When the 3D endoscope 5 is used, an operator usually performs a surgery or the like in a state of 2D observation and switches the 2D observation to 3D observation in a situation that an accurate treatment or the like is necessary. Therefore, the 3D mixer 9 generates a 3G-SDI signal corresponding to the HD double-speed 3D video signal (abbreviated as double-speed 3D video signal in some cases) and the HD double-speed 2D video signal (abbreviated as double-speed 2D video signal in some cases). Note that it can be stated that the HD double-speed 3D video signal is a high-definition 3D video signal as in the case of the HD 3D video signal. It can be stated that the HD double-speed 2D video signal is a high-definition 2D video signal as in the case of the HD 2D video signal.

In the 3G-SDI signal, ancillary data as ancillary information including a payload ID or the like as identification information indicating whether a video signal part of the 3G-SDI signal is a high-definition 3D video signal or a high-definition 2D video signal is added to a head part of the video signal. That is, the 3D mixer 9 generates a 3G-SDI signal provided with a high-definition 3D/2D video signal and ancillary data including identification information indicating identification of 3D/2D in the head part. A first 3D monitor 11A configured to receive the 3G-SDI signal through a wire is a 3D monitor 11A capable of displaying a video corresponding to the 3G-SDI signal, and the first 3D monitor 11A identifies the identification information in the input signal to display a 3D video and a 2D video.

The stereoscopic endoscope system 1 includes: the first 3D monitor 11A provided on the trolley 6 in which the 3G-SDI signal generated by the 3D mixer 9 is inputted through a wire as described above; and a second 3D monitor 11B attached to a monitor support table 12 in a movable manner. As described, the first 3D monitor 11A is a 3D monitor having a display function corresponding to the 3G-SDI signal, and the same applies to the second 3D monitor 11B.

The stereoscopic endoscope system 1 further includes: a wireless transmission section (or wireless communication apparatus) 13 provided on the trolley 6 and configured to transmit, to the second 3D monitor 11B, the video signal and the ancillary data including the payload ID as an identification ID for distinguishing whether the video signal is a 3D video signal or a 2D video signal; and a wireless reception section (or wireless reception apparatus) 14 arranged near the second 3D monitor 11B and configured to receive the video signal and the ancillary data transmitted by the wireless transmission section 13 without a wire (wirelessly).

In the present embodiment, the 3D mixer 9 generates a 3G-SDI signal when the 3D endoscope 5 is adopted. On the other hand, when a 2D endoscope not shown is adopted, the 3D mixer 9 is not used, and one of the processors 8A and 8B outputs, as an output signal, an HD-SDI signal or an SD-SDI signal to the first 3D monitor 11A and the wireless transmission section 13. Note that when the 2D endoscope is adopted, the 3D mixer 9 may ignore the input signal from one of the processors 8A and 8B, and the signal may be outputted as an output signal.

The stereoscopic endoscope system 1 further includes, for example, polarization glasses 15A and 15B for, for example, operators D1 and D2 that perform a surgery to visually check a 3D video based on the 3D video (pseudo 3D video formed by left and right 2D videos) (or 3D images) displayed on the first 3D monitor 11A and the second 3D monitor 11B, respectively.

An electric knife 16 for example is inserted into an abdominal part of the patient 4, and the electric knife 16 is connected to an electric knife power source apparatus 17 mounted on the trolley 6 through a cable 18.

The wireless transmission section 13 and the wireless reception section 14 form a wireless transfer system 19 of a first embodiment. Note that the wireless transfer system of the present invention may include at least the wireless transmission section 13 and the wireless reception section 14 and may further include other medical devices and the like shown in FIG. 1. For example, the stereoscopic endoscope system 1 of FIG. 1 may form the wireless transfer system of the present invention.

The 3D endoscope 5 is detachably connected to the light source apparatus 7 and the first and second processors 8A and 8B through a universal cable 21 or the like. Note that a peripheral region including the bed 3 is a sterile area Rc subjected to a sterilization process as shown in FIG. 1, and a peripheral region separate from the sterile area Rc and including a position provided with the trolley 6 is a non-sterile area Rn. A region provided with the monitor support table 12 is also a non-sterile area Rn.

The operators D1 and D2 in the sterile area Rc cannot directly operate the medical devices mounted on the trolley 6 arranged in the non-sterile area Rn. Therefore, to operate the medical devices, the operators D1 and D2 use voice or the like to instruct a nurse or the like not shown located in the non-sterile area Rn to operate the medical devices.

In the present embodiment, when the operators D1 and D2 in the sterile area Rc want to switch the 3D observation and the 2D observation during the surgery, the operators D1 and D2 can operate a change-over switch 78 provided on the polarization glasses 15A or 15B worn by the operators D1 and D2 to wirelessly send a switch instruction signal to the 3D mixer 9 as described later. Note that a microphone may be provided in place of the change-over switch 78, and the microphone may convert voice generated by the operators D1 and D2 into a voice signal. A wireless transmitter 79 may wirelessly transmit the voice signal to perform the switching on the 3D mixer 9 side. In this case, a voice recognition circuit configured to perform voice recognition of the voice signal received by a wireless receiver 46 may be provided to recognize (identify) the switching of the 3D observation and the 2D observation based on the voice.

That is, the present embodiment includes 3D/2D instruction operation means or 3D/2D switch instruction operation means configured to allow the operators D1 and D2 in the sterile area Rc to easily switch (select) the high-definition 3D video and the high-definition 2D video from the inside of the sterile area Rc.

Figure 2:
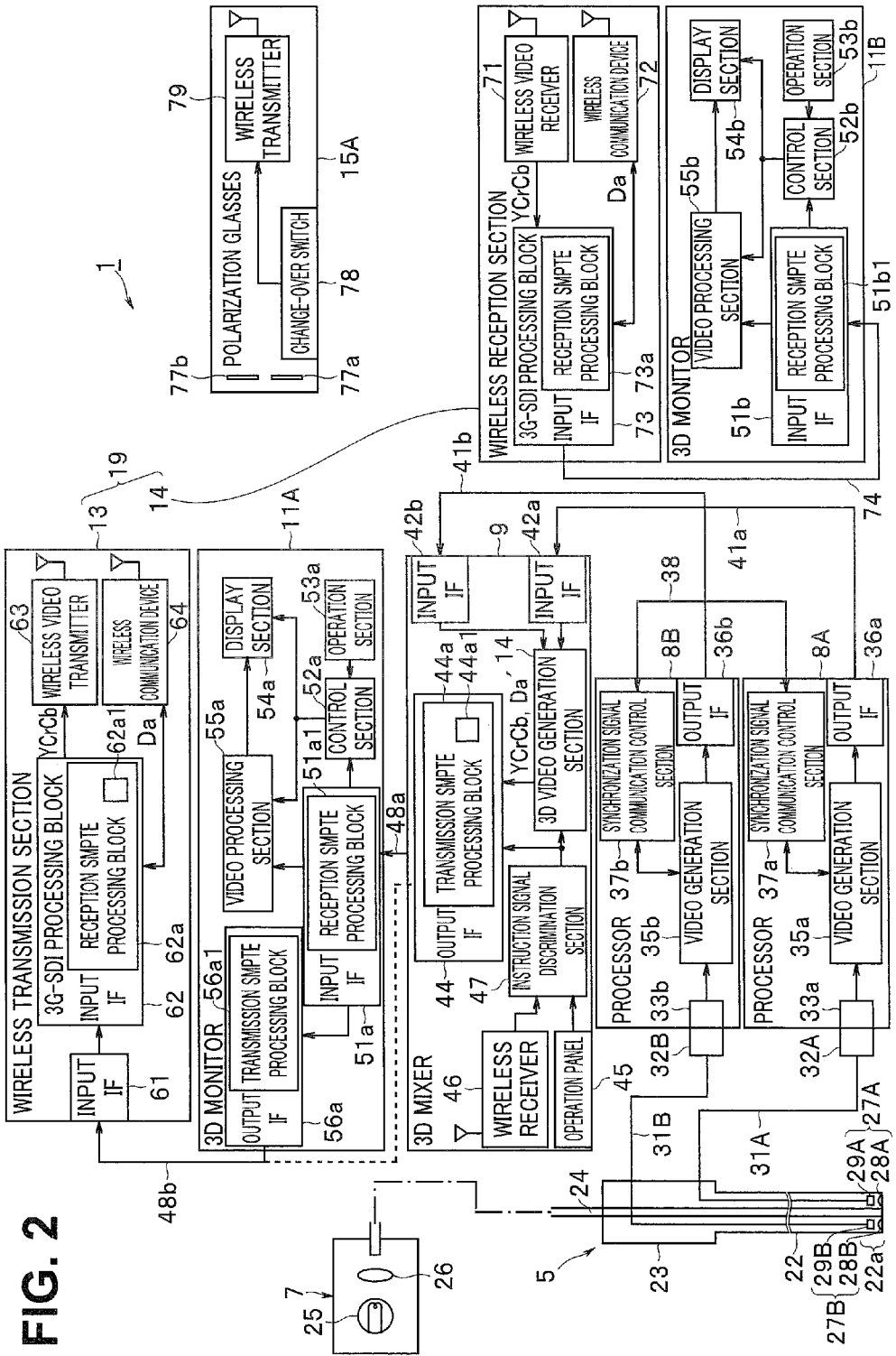
FIG. 2 is a diagram showing an internal configuration of main medical devices in FIG. 1.

FIG. 2 shows a configuration of main parts of FIG. 1.

The 3D endoscope 5 includes an elongated insertion portion 22 and a grasping portion 23 provided on a rear end (proximal end) of the insertion portion 22. A light guide 24 for transferring illumination light is inserted into the insertion portion 22, and a proximal end of the light guide 24 is connected to the light source apparatus 7 through the universal cable 21 extended from the grasping portion 23.

The light source apparatus 7 includes: a lamp 25 configured to generate illumination light; and a condensing lens 26 for condensing the illumination light generated by the lamp 25 to cause the illumination light to enter the proximal end of the light guide 24. The illumination light entering the proximal end of the light guide 24 is transferred to a distal end surface of the light guide 24. The distal end surface of the light guide 24 is attached to an illuminating window provided on a distal end portion 22a of the insertion portion 22, and the transferred illumination light is emitted to the outside from the illuminating window to illuminate a subject such as a diseased part.

The first image pickup section 27A and the second image pickup section 27B as a pair of two image pickup sections (or image pickup devices) adjacent to the illumination window are provided on the distal end portion 22a of the insertion portion 22, separately in a horizontal direction. The first image pickup section 27A and the second image pickup section 27B include objective lenses 28A and 28B and, for example, charge-coupled devices (abbreviated as CCDs) 29A and 29B as solid-state image pickup devices arranged at image formation positions of the objective lenses 28A and 28B, respectively.

The objective lenses 28A and 28B included in the first image pickup section 27A and the second image pickup section 27B form optical images of the illuminated subject, such as a diseased part, on image pickup surfaces of the CCDs 29A and 29B, and the CCDs 29A and 29B output respective photoelectrically converted image pickup signals.

CCDs with a large number of pixels are used as the CCDs 29A and 29B to allow generating a high-definition (HD) video. As described above, the processors 8A and 8B generate left and right HD 2D video signals, and the 3D mixer 9 generates, from the left and right HD 2D video signals, a 3G-SDI signal for displaying a 3D/2D video with a signal transfer rate twice as fast as (also called double-speed) an HD-SDI (serial digital interface) signal.

The 3D monitors 11A and 11B are 3D monitors corresponding to the 3G-SDI signal, and when the 3G-SDI signal is inputted, the 3D monitors 11A and 11B generate a video signal for progressive display, on a display surface, of a video with 1920×1080 (width×height) pixels for a resolution of width×height, at a 60 frames/S (1920×1080p, or simple expression of 1080p or 1080/60p).

Note that the HD-SDI signal has a transfer rate of 1.486 Gb/S, and the 3G-SDI has a signal transfer rate of 2.97 Gb/S (almost 3 Gb/S).

Since the first image pickup section 27A and the second image pickup section 27B are arranged separately in the horizontal direction, the first image pickup section 27A and the second image pickup section 27B generate signals (image pickup signals) of a left pickup video (left pickup image) and a right pickup video (right pickup image) picked up from a left side and a right side, respectively, when a common subject is imaged. Therefore, the first image pickup section 27A and the second image pickup section 27B will also be called a left image pickup section and a right image pickup section. In the CCDs 29A and 29B included in the left and right image pickup sections, respectively, signal connectors 32A and 32B provided on end portions of signal lines 31A and 31B are detachably connected to signal connector receivers 33a and 33b of the first and second processors 8A and 8B, respectively, through the signal lines 31A and 31B, respectively.

The first and second processors 8A and 8B include: video signal generation sections (or video signal generation circuits) 35a and 35b configured to generate left and right 2D video signals from the left and right image pickup signals inputted from the left and right image pickup sections; video output interfaces (abbreviated as video output IFs, also written as output IFs in the drawings) 36a and 36b configured to output the generated left and right video signals; and synchronization signal communication control sections (or synchronization signal communication control circuits) 37a and 37b configured to synchronize the left and right video signals.

The synchronization signal communication control sections 37a and 37b are connected through a communication line 38 and perform control to synchronize one synchronization signal to the other synchronization signal. Therefore, the first and second processors 8A and 8B are in a state that the video signal generation sections 35a and 35b output mutually synchronized left and right 2D video signals.

As described, when the CCDs 29A and 29B are CCDs with a large number of pixels, the video signal generation sections 35a and 35b generate high-definition (HD) left and right 2D video signals, respectively, and output the signals to the 3D mixer 9.

The present embodiment also corresponds to a case in which a 2D endoscope including one image pickup section configured to generate a high-definition (HD) or standard video (SD) is used. In the case of the HD or SD 2D endoscope, the video signal generation section of one of the first and second processors 8A and 8B generates an HD or SD 2D video signal (that is, HD-SDI signal or SD-SDI signal) and outputs the signal to the first monitor 11A and the wireless transmitter 13 by ignoring the 3D mixer 9.

The left and right HD 2D video signals outputted from the video output IFs 36a and 36B, respectively, are inputted to video input IFs 42a and 42b of the 3D mixer 9 through signal lines 41a and 41b (when the 3D endoscope 5 is used).

The 3D mixer 9 includes: the video input IFs 42a and 42b; and a 3D video generation section (or 3D video generation circuit) 43 configured to generate an (HD) double-speed 3D video signal from the left and right HD 2D video signals inputted through the video input IFs 42a and 42b (more specifically, a Y/color difference component signal with resolution of 1920×1080p, the Y/color difference component signal of 1920×1080p will be abbreviated as a YCrCb signal of 1080p, or more simply, a YCrCb signal).

The 3D mixer 9 further includes: a video output IF 44 configured to output the double-speed 3D video signal generated by the 3D video generation section 43; an operation panel 45 for performing operation for 3D/2D observation by the 3D endoscope 5 (based on 3G-SDI signal), switch operation of the 3D/2D observation, and the like; the wireless receiver 46 configured to receive the switch signal of the 3D observation or the 2D observation wirelessly transmitted from the polarization glasses 15A or 15B; and an instruction signal discrimination section (or instruction signal discrimination circuit) 47 configured to discriminate whether the signal is a 3D observation instruction signal or a 2D observation instruction signal with reference to an operation instruction signal based on the operation of the operation panel 45 or with reference to a received switch instruction signal. Note that the Y/color difference component signal of 1920×1080p is equivalent to the double-speed 3D video signal in some cases and is equivalent to the double-speed 2D video signal in other cases. Note that the former is an HD video signal for displaying a 3D video of 1920×1080i+1920×1080i as shown in step S41 of FIG. 12 described later, and the latter is an HD video signal for displaying a 2D video of 1920×1080p as shown in S39.

When an operation switch 45a of the operation panel 45 for performing 3D/2D observation is operated, the instruction signal discrimination section 47 outputs an instruction signal of the operation to the 3D video generation section 43 and the video output IF 44. The 3D video generation section 43 generates a double-speed 3D/2D video signal corresponding to the high-definition 3D/2D observation and outputs the signal to the video output IF 44.

The 3D video generation section 43 includes: a double-speed 3D/2D video signal generation circuit 43a configured to generate a double-speed 3D/2D video signal (YCrCb signal of 1080p); and an ancillary data generation circuit 43b configured to output (generate) ancillary data Da' into which a payload ID is inserted (hereinafter, identification ID will be used). As shown in FIG. 2, the 3D video generation section 43 outputs the generated YCrCb signal that is a double-speed 3D/2D video signal and the ancillary data Da' to the video output IF 44. Note that the ancillary data Da' here is ancillary data not including the identification ID, and when the identification ID is inserted into the ancillary data Da' based on a discrimination result of the switch signal of the 3D observation or the 2D observation of the instruction signal discrimination section 47 as described below, the ancillary data Da' becomes ancillary data Da.

The video output IF 44 includes a transmission SMPTE processing block 44a as a transmission signal processing block configured to execute a process of generating a 3G-SDI signal by adding the ancillary data Da indicating a signal standard or the like to a head part of the video signal part when the double-speed 3D/2D video signal (YCrCb signal) is inputted.

The video output IF 44 outputs the 3G-SDI signal generated by the transmission SMPTE processing block 44a to the 3D monitor 11A through a coaxial cable 48a.

The video output IF 44 also outputs the signal to the wireless transmission section 13 through a coaxial cable 48b. Note that when the 3D monitor 11A includes a video output IF 56a as shown in FIG. 2, the 3G-SDI signal or the like may be outputted to the wireless transmission section 13 from a video input IF 51a, through the video output IF 56a, and through the coaxial cable 48b connected to the video output IF 56a, as indicated by solid lines in FIG. 2.

The video output IF 56a includes a transmission SMPTE processing block 56a1 as a transmission signal processing block having a same processing function as the transmission SMPTE processing block 44a described in the 3D mixer 9. The 3G-SDI signal may be outputted to the wireless transmission section 13 from the 3D mixer 9 through the coaxial cable 48b as indicated by a dotted line in FIG. 2, without using the video output IF 56a.

The ancillary data Da includes an identification ID serving as identification information for distinguishing whether the video data (also called picture data) in the 3G-SDI signal is a 3D video or a 2D video.

In the present embodiment, a change-over switch 45b (see FIG. 4) provided on the operation panel 45 and configured to perform switch operation of the 3D observation and the 2D observation is operated, and the 3D video generation section 43 outputs a double-speed 3D/2D video signal corresponding to the switch operation to the transmission SMPTE processing block 44a of the video output IF 44. The transmission SMPTE processing block 44a executes a process of arranging (inserting), in the ancillary data Da, the identification ID corresponding to the switch instruction operation of the 3D observation and the 2D observation of the change-over switch 45b. That is, the transmission SMPTE processing block 44a has a function of an identification ID insertion processing block 44a1 configured to execute a process of inserting the identification ID.

Note that as described later, a wirelessly transmitted switch instruction signal is also inputted to the instruction signal discrimination section 47 through the wireless receiver 46 when the change-over switch 78 provided on the polarization glasses 15A or 15B is operated. In this case, the transmission SMPTE processing block 44a similarly executes a process of arranging (inserting), in the ancillary data, the identification ID corresponding to the switch instruction operation of the 3D observation and the 2D observation of the change-over switch 45b.

As described in operation described later, the transmission SMPTE processing block 44a (identification ID insertion processing block 44a1) executes a process of inserting an identification ID of Level A (level A) into the ancillary data when the switch instruction signal indicates the 2D observation instruction and executes a process of inserting an identification ID of Level B (level B) into the ancillary data when the switch signal indicates the 3D observation instruction.

Note that when a 2D endoscope that is not the 3D endoscope 5 is used, the 3D video generation section 43 of the 3D mixer 9 outputs the HD/SD 2D video signal inputted from one of the video input IFs to the video output IF 44 without change, and the video output IF 44 outputs the HD/SD 2D video signal without change, without adding the identification ID. As described above, the 3D mixer 9 is not necessary when the 2D endoscope is used.

Figure 3:
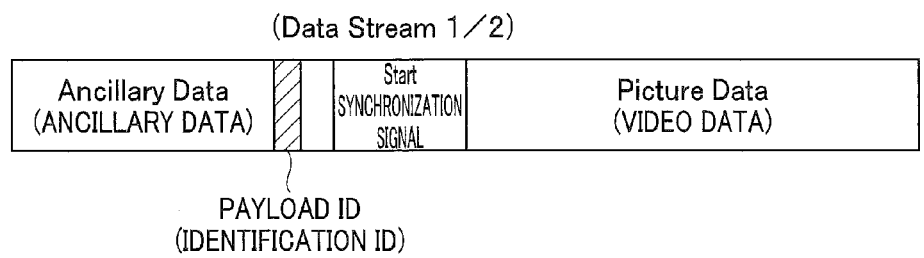
FIG. 3 is a diagram showing a data configuration of one horizontal line of a 3G-SDI signal.

FIG. 3 shows a data structure (Data Stream 1 or 2) of one horizontal line in 1080/60p in the 3G-SDI signal generated by the transmission SMPTE processing block 44a adding the identification ID to the double-speed 3D/2D video signal when the 3D endoscope 5 is used.

As shown in FIG. 3, Ancillary Data (ancillary data) Da is added to a header part of Start (start part of synchronization signal) St and Picture Data (video data) Dv, and an identification ID 49 for distinguishing whether the video data Dv is a 3D video or a 2D video is arranged at a predetermined position in the ancillary data Da.

In one Data Stream in FIG. 3, one horizontal line including only the start part St of the synchronization signal and the video data Dv part is a signal format part equivalent to the HD-SDI signal.

The signal transfer rate of the HD-SDI signal is ½ of that of the 3G-SDI signal, and a serial clock frequency is 1.485 GHz. In other words, the 3G-SDI signal has a signal format including two Data Stream structures, in which respective ancillary data Da are added to the header parts of the video data Dv parts of two horizontal lines (including the synchronization signal start parts St) in the HD-SDI signal, and the speed is doubled.

In the 3G-SDI signal, the data is transferred in order of Data Stream 2→Data Stream 1→Data Stream 2 . . . .

In this case, Data Stream 1 and Data Stream 2 have same data when the signal is a 2D video signal.

On the other hand, when the signal is a 3D video signal, a signal format is a video signal of 1080/60p including one interlaced video signal of left eye data 1080/60i and another interlaced video signal of right eye data 1080/60i.

Figure 4:
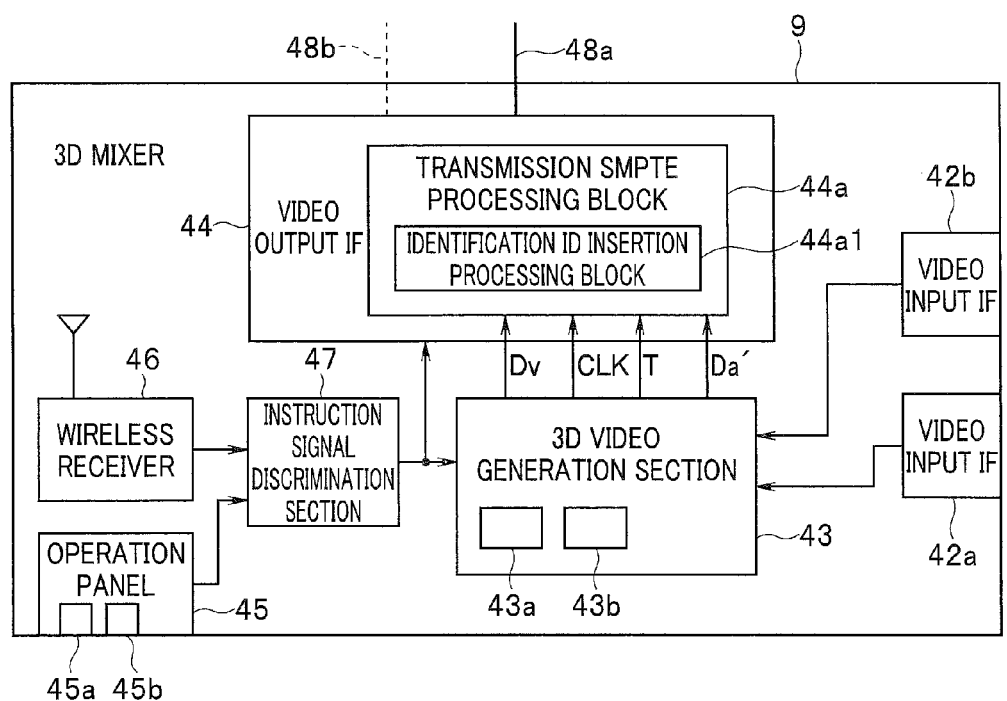
FIG. 4 is a block diagram showing a 3D video generation section configured to generate a 3G-SDI signal and a video output IF in a 3D mixer.

FIG. 4 illustrates an enlarged configuration of the 3D mixer 9 of FIG. 2. When the 3D endoscope 5 of FIG. 2 is used, the 3D video generation section 43 forwards the video data Dv, a clock CLK, a timing signal T, and the ancillary data Da' equivalent to a double-speed 3D/2D video signal (YCrCb signal of 1080p) to the transmission SMPTE processing block 44a, and the transmission SMPTE processing block 44a converts the signal to a 3G-SDI signal.

Note that the video data Dv, the clock CLK, and the timing signal T are mixed to form the double-speed 3D/2D video signal (YCrCb signal of 1080p).

The transmission SMPTE processing block 44a uses the YCrCb signal and the ancillary data Da' to convert the signal to the 3G-SDI signal. As described, the ancillary data Da' does not include the identification ID, and the transmission SMPTE processing block 44a inserts the identification ID into the ancillary data Da' to generate the ancillary data Da including the identification ID.

The transmission SMPTE processing block 44a also adds the ancillary data Da to the head part of the double-speed 3D/2D video signal (YCrCb signal of 1080p) inputted from the 3D video generation section 43 to arrange a 3G-SDI data structure as shown in FIG. 3. As shown in FIG. 3, the identification ID for identifying the (double-speed) 3D or 2D video signal is inserted into the ancillary data Da.

As described, the 3D video generation section 43 generates the double-speed 3D or 2D video signal according to the 3D or 2D observation instruction signal in the present embodiment, and the transmission SMPTE processing block 44a (identification ID insertion processing block 44a1 of the transmission SMPTE processing block 44a) inserts the identification ID as an identification ID indicating the double-speed 3D or 2D video signal into the ancillary data Da according to the 3D or 2D observation instruction signal.

The output signal of the 3D mixer 9 is inputted to the 3D monitor 11A arranged on the trolley 6 through the coaxial cable 48a and is inputted to the wireless transmission section 13 arranged near the trolley 6 or the 3D monitor 11A through the coaxial cable 48b (through the video output IF 56a in the 3D monitor 11A, or without the involvement of the video output IF 56a).

As shown in FIG. 2, the 3D monitor 11A includes: the video input IF 51a to which a video signal of 3G-SDI or the like is inputted; a control section (or control circuit) 52a configured to control display; an operation portion (or operation panel) 53a for the user to perform operation of setting the display or the like; a display section (or display device) 54a configured to display a 3D/2D video; and a video processing section (or video processing circuit) 55a configured to execute signal processing for displaying a video on the display section 54a. There is also a 3D monitor including the output IF 56a as in the 3D monitor 11A shown in FIG. 2.

Figure 5:
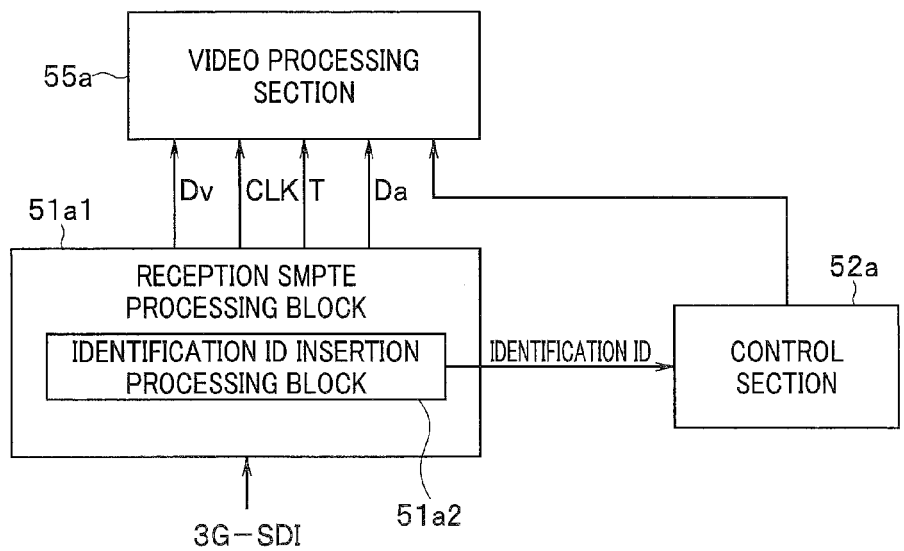
FIG. 5 is a diagram showing a configuration of a peripheral portion of a reception SMPTE processing block in the 3D monitor.

The video input IF 51a includes a reception SMPTE processing block 51a1 as a reception signal processing block configured to execute a process corresponding to the 3G-SDI signal. FIG. 5 shows a process in the reception SMPTE processing block 51a1 of FIG. 2 when the 3G-SDI signal is inputted.

As shown in FIG. 5, when the 3G-SDI signal is inputted, the reception SMPTE processing block 51a1 executes a process of separating the signal into the video data Dv, the clock CLK, and the timing signal T equivalent to the double-speed 3D or 2D video signal (YCrCb signal of 1080p) and the ancillary data Da. That is, the reception SMPTE processing block 51a1 has a function of a separation circuit configured to separate the 3G-SDI signal into the video signal and the ancillary data Da.

The reception SMPTE processing block 51a1 outputs the separated video data Dv, clock CLK, timing signal T, and ancillary data Da to the video processing section 55a and outputs the identification ID extracted from the ancillary data Da to the control section 52a. The reception SMPTE processing block 51a1 has a function of an identification ID extraction processing block 51a2 configured to extract the identification ID as an identification ID from the ancillary data.

The video processing section 55a generates a video signal for displaying the video data Dv separated by the reception SMPTE processing block 51a1 as a 3D/2D video in the display section 54a, and the display section 54a displays a high-definition 3D/2D video.

The control section 52a controls the operation of the video processing section 55a and the display section 54a according to the identification ID. More specifically, when the identification ID is an ID indicating a 3D video, the control section 52a controls the video processing section 55a to generate a high-definition 3D video signal, and the display section 54a displays a high-definition 3D video. When the identification ID is an ID indicating a 2D video, the control section 52a controls the video processing section 55a to generate a high-definition 2D video signal, and the display section 54a displays a high-definition 2D video.

Figure 6A:
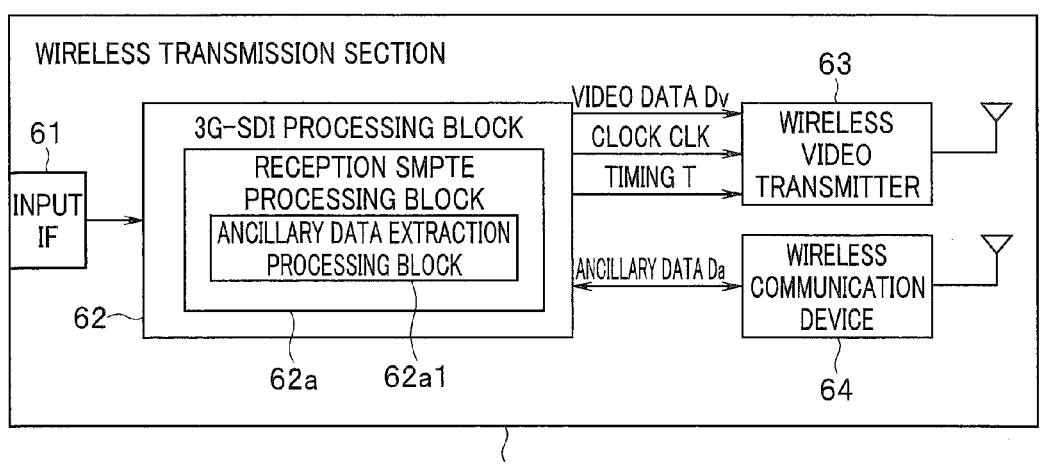
FIG. 6A is a block diagram showing a configuration of a wireless transmission section in FIG. 2.

As shown in FIG. 2 or FIG. 6A, the wireless transmission section 13 includes: a video input IF 61 forming an input section to which an input signal is inputted; a 3G-SDI processing block 62 configured to execute a process corresponding to the case in which the input signal is a 3G-SDI signal or the like; a wireless video transmitter 63 configured to wirelessly transmit a double-speed 3D/2D video signal (YCrCb) extracted by the 3G-SDI processing block 62; and a wireless communication device 64 configured to use a frequency different from a frequency for the wireless transmission by the wireless video transmitter 63 to execute a process of wirelessly transmitting the ancillary data Da including the identification ID extracted by the 3G-SDI processing block 62. Note that the wireless communication device 64 includes a wireless transmitter/receiver for two-way wireless communication.

The 3G-SDI processing block 62 includes a reception SMPTE processing block 62a, and when the 3G-SDI signal is inputted, the reception SMPTE processing block 62a executes a process of separating the 3G-SDI signal into the double-speed 3D/2D video signal (YCrCb) including the video data Dv, the clock CLK, and the timing (signal) T and the ancillary data Da as shown in FIG. 6A.

As shown in FIG. 6A, the reception SMPTE processing block 62a outputs the separated video data Dv, clock CLK, and timing signal T to the wireless video transmitter 63 and outputs the ancillary data Da to the wireless communication device 64.

The ancillary data Da in this case is ancillary data including the identification ID. Therefore, the reception SMPTE processing block 62a includes an ancillary data extraction processing block 62a1 configured to extract the ancillary data including the identification ID from the 3G-SDI signal.

Figure 6B:
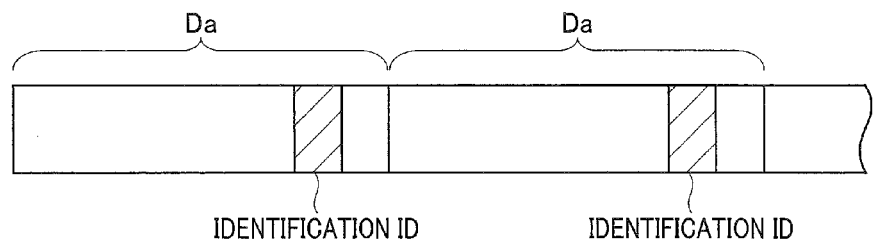
FIG. 6B is a diagram showing that ancillary data includes an identification ID.

The ancillary data Da outputted to the wireless communication device 64 includes the identification ID as shown in FIG. 6B.

Figure 7:
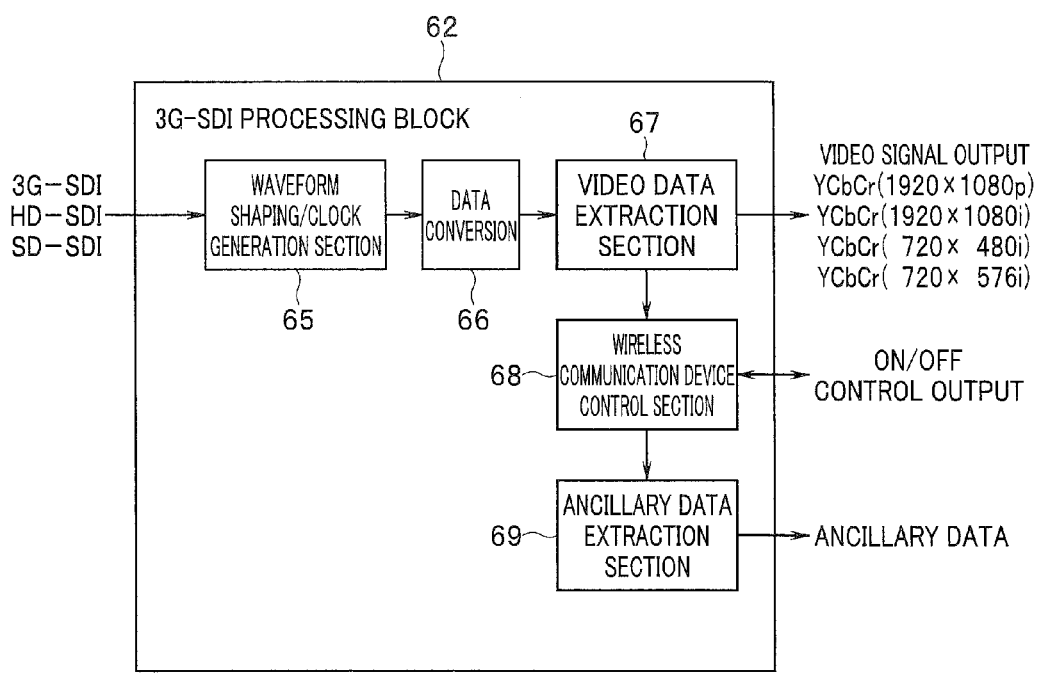
FIG. 7 is a block diagram showing a configuration of a 3G-SDI processing block of FIG. 6A.

The 3G-SDI processing block 62 shown in FIG. 6A may have a configuration as shown in FIG. 7.

As shown in FIG. 7, the 3G-SDI processing block 62 includes: a waveform shaping/clock generation section 65 configured to shape a waveform of the input signal and to generate a clock with a shaped waveform; a data conversion section (or data conversion circuit or data separation section) 66 configured to use the generated clock to perform data conversion (separation) for separating the video data and the ancillary data from the input signal with the shaped waveform; a video data extraction section (or video data extraction circuit) 67 as a video signal extraction section configured to extract video (signal) data from the data separated by the data conversion section 66; a wireless communication device control section (or wireless communication device control circuit) 68 configured to control transmission operation of at least the wireless communication device 64 based on whether the data is a 3G-SDI signal or whether the data includes ancillary data or identification ID; and an ancillary data extraction section (or ancillary data extraction circuit) 69 as an ancillary information extraction section configured to extract the ancillary data Da including the identification ID from the data. The ancillary data extraction section 69 extracts the ancillary data Da only when the 3G-SDI signal includes the ancillary data Da.

As shown in FIG. 7, one of the 3G-SDI signal, the HD-SDI signal, and the SD-SDI signal is inputted to the 3G-SDI processing block 62. The 3G-SDI signal is a first video signal compliant with a first signal transfer standard provided with the ancillary information including the identification information, and the HD-SDI signal or the SD-SDI signal forms a second video signal compliant with a second signal transfer standard with a signal transfer rate lower than that of the first signal transfer standard and not including the identification information.

When the 3G-SDI signal is inputted, the video data extraction section 67 outputs, as a video signal, YCbCr that is a Y/color difference component signal with the resolution of 1920×1080p to the wireless video transmitter 63. The wireless communication device control section 68 controls the wireless communication device 64 to enter an operation state (ON control) of performing communication in order to transmit the ancillary data Da. The wireless communication device control section 68 also controls the wireless communication device 64 to wirelessly transmit, along with the ancillary data Da, an ON control signal for putting a wireless communication device 72 into an operation state (ON control) for performing communication.

On the other hand, when the HD-SDI signal is inputted, the video data extraction section 67 outputs, as a video signal, YCbCr that is a Y/color difference component signal with the resolution of 1920×1080i to the wireless video transmitter 63.

Since there is no need to transmit the ancillary data Da, the wireless communication device control section 68 controls the wireless communication device 64 to enter an operation stop state (OFF control) for stopping the operation of performing the communication.

When the SD-SDI signal is inputted, the video data extraction section 67 outputs, as a video signal, YCbCr that is a Y/color difference component signal with the resolution of 720×480i or 720×576i to the wireless video transmitter 63. As in the case of the HD-SDI signal, the wireless communication device control section 68 controls the wireless communication device 64 to enter the operation stop state (OFF control) for stopping the operation of performing the communication.

The wireless reception section 14 shown in FIG. 2 includes: a wireless video receiver 71 configured to receive a video signal wirelessly transmitted from the wireless video transmitter 63; a wireless communication device 72 configured to wirelessly communicate with the wireless communication device 64 to receive the ancillary data Da wirelessly transmitted from the wireless communication device 64; and a 3G-SDI processing block 73 configured to execute a process of generating a 3G-SDI signal from the video signal received by the wireless video receiver 71 and the ancillary data Da received by the wireless communication device 72.

The wireless video receiver 71 outputs the double-speed 3D/2D video signal (YCrCb) as a received video signal to the 3G-SDI processing block 73 in the case of the 3D/2D observation, and the wireless communication device 72 outputs the received ancillary data Da to the 3G-SDI processing block 73. The 3G-SDI processing block 73 generates a 3G-SDI signal from the double-speed 3D/2D video signal (YCrCb) and the ancillary data Da and outputs the generated 3G-SDI signal to the 3D monitor 11B attached to the monitor support table 12 through a coaxial cable 74.

Note that the 3D monitor 11B has the same configuration as the 3D monitor 11A on the trolley 6 side. Reference signs ○○a are written as ○○b for the same constituent elements as in the 3D monitor 11A, and the description will not be repeated. However, a 3D monitor 11B with a structure not including a video output IF 56b is illustrated in FIG. 2.

Figure 8:
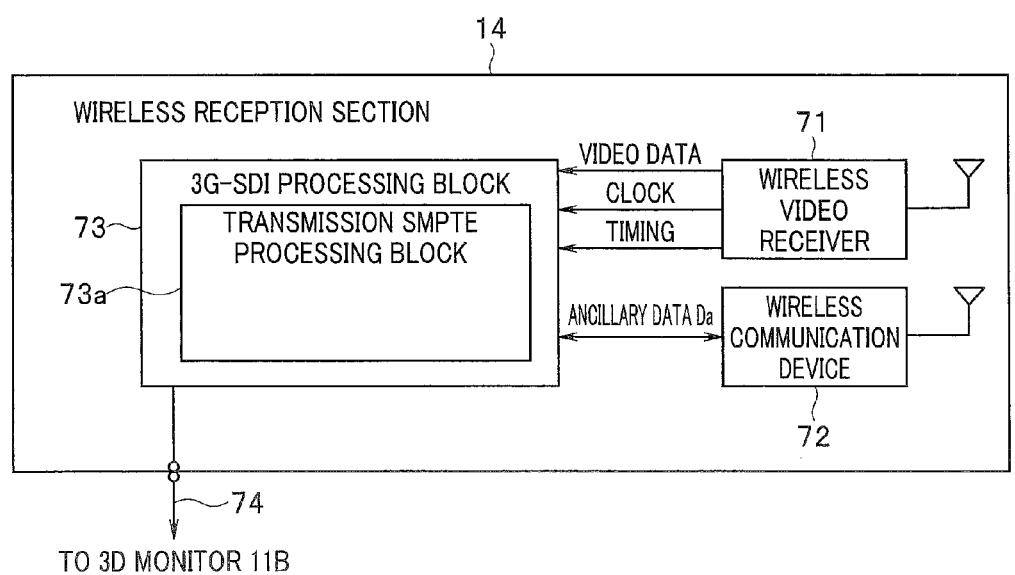
FIG. 8 is a block diagram showing a configuration of a wireless reception section of FIG. 2.

As shown in FIG. 8, the wireless reception section 14 outputs the video data Dv, the clock CLK, and the timing (signal) T (forming the double-speed 3D/2D video signal (YCrCb) shown in FIG. 2) to the 3G-SDI processing block 73, and the wireless communication device 72 outputs the ancillary data Da to the 3G-SDI processing block 73.

The 3G-SDI processing block 73 includes a transmission SMPTE processing block 73a configured to execute a process of generating a 3G-SDI signal from the video data Dv, the clock CLK, and the timing T from the wireless reception section 14 and the ancillary data Da from the wireless communication device 72.

Note that since the wireless communication device 64 wirelessly transmits the ancillary data Da including the identification ID as described above, the ancillary data Da inputted to the transmission SMPTE processing block 73 from the wireless communication device 72 that has received the ancillary data Da wirelessly transmitted by the wireless communication device 64 includes the identification ID.

The 3G-SDI processing block 73 (transmission SMPTE processing block 73a of the 3G-SDI processing block 73) generates a 3G-SDI signal as shown in FIG. 3 including the identification ID and outputs (forwards) the signal to the 3D monitor 11B through the coaxial cable 74.

In the present embodiment, the polarization glasses 15A worn by the operator D1 include: left and right polarization plates 77a and 77b; the change-over switch 78 for generating a switch signal; and the wireless transmitter 79 forming a 3D/2D instruction operation transmission section (or 3D/2D instruction operation transmission circuit) configured to wirelessly transmit a switch instruction signal of the change-over switch 78.

The operator can operate the change-over switch 78 to wirelessly transmit a switch instruction signal for switching the 3D observation to the 2D observation or switching the 2D observation to the 3D observation to the 3D mixer 9. Note that the other polarization glasses 15B have the same configuration as the polarization glasses 15A, and the description will not be repeated.

The wireless transfer system 19 of the present embodiment includes: the wireless transmission section 13 forming a wireless transmission section including: the input IF 61 forming an input section configured to receive one of a first video signal and a second video signal as an input signal, the first video signal being compliant with a first signal transfer standard provided with, at a head part of a high-definition video signal, ancillary information including at least identification information indicating one of a high-definition 3D video signal and a high-definition 2D video signal, the second video signal having a signal transfer rate lower than the first video signal and being compliant with a second signal transfer standard not including the identification information; the video data extraction section 67 forming a video signal extraction section configured to extract one of the high-definition video signal and the second video signal from the input signal; the ancillary data extraction section 69 forming an ancillary information extraction section configured to extract the ancillary information including at least the identification information from the input signal; the wireless video transmitter 63 configured to wirelessly transmit one of the high-definition video signal and the second video signal extracted by the video signal extraction section; the wireless communication device 64 as a wireless ancillary information transmitter configured to wirelessly transmit the ancillary information extracted by the ancillary information extraction section in a band different from a band for the wireless transmission by the wireless video transmitter 63; and the wireless communication device control section 68 forming a control section configured to control operation of the wireless ancillary information transmitter according to an extraction result of the ancillary information; and the wireless reception section 14 as a wireless reception section including: the wireless video receiver 71 configured to receive one of the high-definition video signal and the second video signal wirelessly transmitted from the wireless video transmitter 63; the wireless communication device 72 as a wireless ancillary information receiver configured to receive the ancillary information wirelessly transmitted from the wireless ancillary information transmitter; and the 3G-SDI processing block 73 forming an output signal control section configured to add the ancillary information to the high-definition video signal and output the high-definition video signal when the ancillary information is received and configured to output the second video signal when the ancillary information is not received, according to a reception result of the wireless video receiver 71 and a reception result of the wireless ancillary information receiver.

Next, operation of the present embodiment will be described. First, operation of the 3D mixer 9 generating a 3G-SDI signal for displaying a high-definition 3D/2D video on the 3D monitor 11A corresponding to the 3G-SDI signal will be described with reference to FIG. 9.

Figure 9:
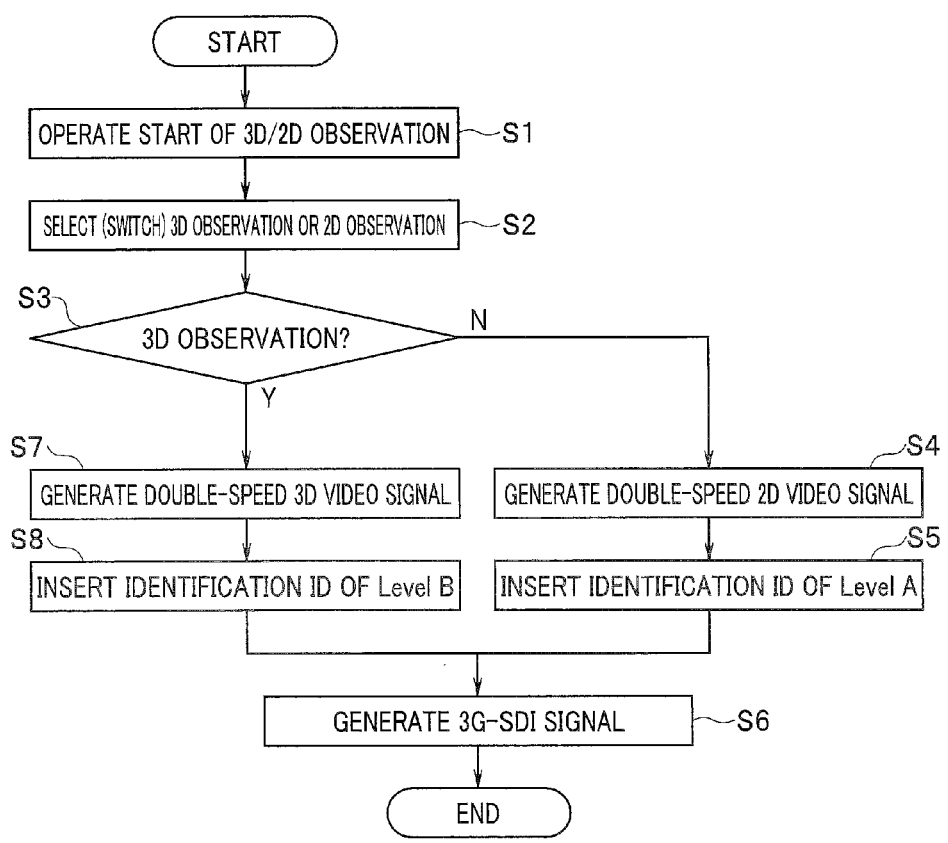
FIG. 9 is a flowchart showing operation of the 3D mixer generating a 3G-SDI signal.

As shown in FIG. 1, when the 3D endoscope 5 is used to perform high-definition 3D or 2D (abbreviated as 3D/2D) observation (utilizing the 3G-SDI signal), a nurse in the non-sterile area operates the operation switch 45a of the operation panel 45 based on, for example, an instruction of the operator D1 or D2 to first set a state for starting the high-definition 3D/2D observation, as shown in step S1 of FIG. 9. The 3D endoscope 5 outputs left and right image pickup signals to the processors 8A and 8B, and the processors 8A and 8B output left and right HD 2D video signals (left and right HD-SDI signals) to the 3D mixer 9.

As shown in step S2, based on the instruction by the operator D1 or D2, the nurse in the non-sterile area performs selection operation (switch operation) for one of the 2D observation and the 3D observation to be performed first by the 3D endoscope 5, from the change-over switch 45b of the operation panel 45, for example.

Consequently, as shown in step S3, the instruction signal discrimination section 47 of the 3D mixer 9 discriminates which one of the 3D observation and the 2D observation is selected (or discriminates switching). For example, the instruction signal discrimination section 47 discriminates whether the 3D observation is selected and outputs a discrimination signal of the 3D observation or the 2D observation to the 3D video generation section 43 and the transmission SMPTE processing block 44a of the video output IF 44.

When the discrimination result indicates that the 2D observation is selected, the 3D video generation section 43 generates a left or right double-speed video signal (left or right double-speed 2D video signal) as shown in step S4.

When the discrimination result indicates that the 2D observation is selected, the transmission SMPTE processing block 44a inserts the identification ID of Level A indicative of the 2D video signal, as an identification ID in the ancillary data Da, as shown in step S5.

In next step S6, the transmission SMPTE processing block 44a generates a 3G-SDI signal from the double-speed 2D video signal and the ancillary data Da into which the identification ID of Level A is inserted.

On the other hand, when the discrimination result indicates that the 3D observation is selected, the 3D video generation section 43 generates left and right double-speed video signals (left and right double-speed 2D video signals) as shown in step S7.

When the discrimination result indicates that the 3D observation is selected, the transmission SMPTE processing block 44a inserts the identification ID of Level B indicative of the 3D video signal, as an identification ID in the ancillary data Da, as shown in step S8. The process proceeds to step S6, and in step S6, the transmission SMPTE processing block 44a generates a 3G-SDI signal from the left and right double-speed video signals and the ancillary data Da into which the identification ID of level B is inserted. The 3D mixer 9 outputs the generated 3 G-SDI signal to the 3D monitor 11A and the wireless transmission section 13.

Note that in relation to the process of step S2, the 2D observation is generally performed in an initial state. Therefore, initial setting may be performed to set an operation state for performing the 2D observation.

Figure 10:
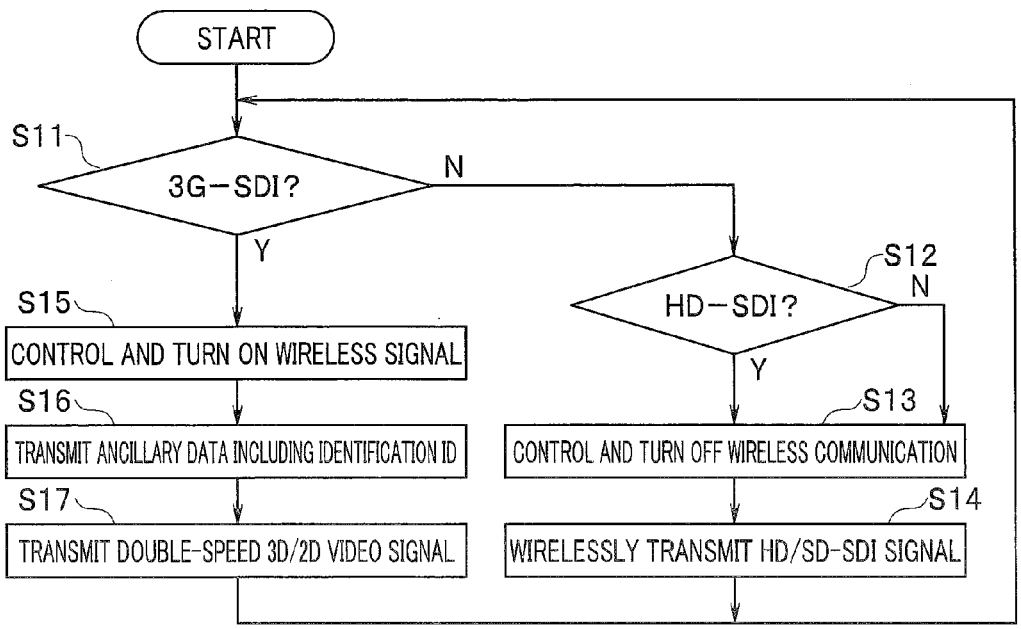
FIG. 10 is a flowchart showing operation of the wireless transmission section transmitting ancillary data including a video signal and an identification ID.

The wireless transmission section 13 to which the 3G-SDI signal or the like is inputted from the 3D mixer 9 operates as in FIG. 10. The operation of the wireless transmission section 13 will be described with reference to FIGS. 7 and 10. As shown in FIG. 7, one of the 3G-SDI signal, the HD-SDI signal, and the SD-SDI signal is inputted to the wireless transmission section 13.

As described in FIG. 7, the process of clock generation by the waveform shaping/clock generation section 65 and the process of data separation by the data conversion section 66 are applied to the video signal as an input signal, and the video signal is then inputted to the video data extraction section 67 and inputted to the wireless communication device control section 68.

As shown in step S11 of FIG. 10, the wireless communication device control section 68 discriminates whether the inputted video signal is a 3G-SDI signal based on, for example, the frequency of the clock of the input signal.

When a discrimination result indicates that the video signal is not the 3G-SDI signal, the wireless communication device control section 68 discriminates whether the video signal is, for example, an HD-SDI signal based on, for example, the frequency of the clock as shown in step S12.

If a discrimination result indicates that the video signal is not the HD-SDI signal, or if the discrimination result indicates that the video signal is not the HD-SDI signal and is an SD-SDI signal with a lower clock frequency, the wireless communication device control section 68 performs control of turning off the communication operation of the wireless communication device 64 as shown in step S13. As a result of the control, the wireless communication device 64 does not communicate with the wireless communication device 72. Therefore, the frequency for the communication between the wireless communication device 64 and the wireless communication device 72 is not used. The wireless communication device 64 can be set to a power saving state by turning off the operation of the wireless communication of the wireless communication device 64. Note that as described later in FIG. 13 and the like, the wireless communication device 64 may transmit a signal for turning off the wireless communication to the wireless communication device 72 to thereby stop the operation of the wireless communication by the wireless communication device 72 through the transmitted signal to also set the wireless communication device 72 to the power saving state.

In next step S14, the wireless video transmitter 63 transmits the HD/SD-SDI signal to the wireless video receiver 71, and after the process of step S14, the process returns to step S11.

In step S11, when the discrimination result indicates that the signal is the 3G-SDI signal, the wireless communication device control section 68 performs control of turning on the communication operation of the wireless communication device 64 as shown in step S15. As a result of the control, the wireless communication device 64 communicates with the wireless communication device 72.

As shown in step S16, the wireless communication device control section 68 wirelessly transmits the ancillary data Da including the identification ID forwarded from the 3D mixer 9 to the wireless communication device 72.

As shown in step S17, the wireless video transmitter 63 wirelessly transmits the double-speed 3D/2D video signal to the wireless video receiver 71. After the process of step S17, the process returns to step S11, and the process described above is repeated.

Figure 11:
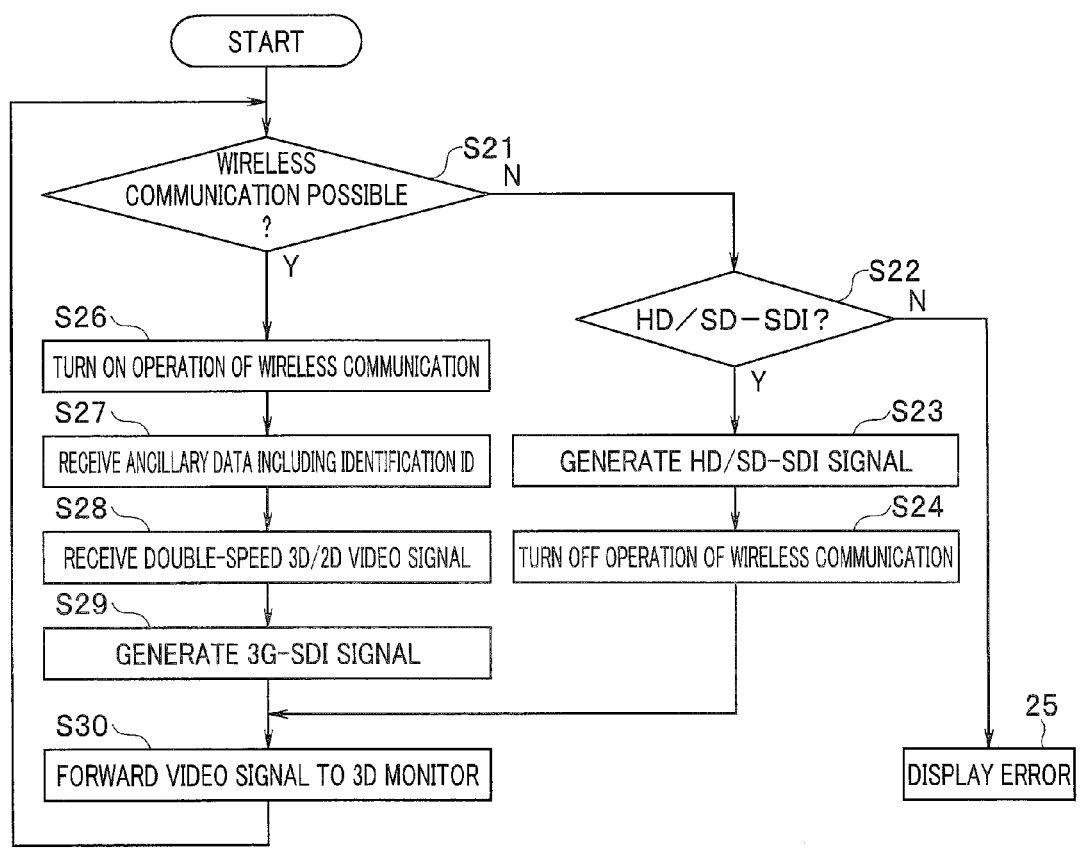
FIG. 11 is a flowchart showing operation of the wireless reception section generating a 3G-SDI signal by receiving the ancillary data including the video signal and the identification ID.

FIG. 11 shows operation of the wireless reception section 14. When the wireless reception section 14 starts the operation, the wireless communication device 72 communicates with the wireless communication device 64 in first step S21 to judge whether a link state that allows wireless communication is established.

In the state of performing the 3D/2D observation using the 3G-SDI signal, the wireless communication device 64 is in the operation state, and the wireless communication device 64 and the wireless communication device 72 are arranged in the same operating room 2. Therefore, if both are in the ON state for performing communication, the communication can be performed. On the other hand, when the 2D endoscope is used, that is, the state is not for performing the 3D/2D observation, the wireless communication device 64 is in the OFF state in which the communication operation is not performed, and the wireless communication device 72 cannot communicate with the wireless communication device 64.

In step S21, when the link state that allows communication is not established, the 3G-SDI processing block 73a discriminates whether the signal is an HD/SD-SDI signal based on the clock frequency of the video signal received by the wireless video receiver 71 as shown in step S22.

When the clock frequency indicates the HD/SD-SDI signal in the discrimination result, the 3G-SDI processing block 73a generates an HD/SD-SDI signal from the video signal received by the wireless video receiver 71 as shown in step S23. As shown in step S24, the 3G-SDI processing block 73a turns off the operation of the wireless communication by the wireless communication device 72. The wireless reception section 14 enters the power saving state in which the operation of the wireless communication of the wireless communication device 72 is turned off.

After the process of step S24, the 3G-SDI processing block 73a forwards the video signal as a generated HD/SD-SDI signal to the 3D monitor 11B through the coaxial cable 74 as shown in step S30. In step S22, when the received video signal is not the HD/SD-SDI signal, a process of displaying an error is executed as shown in step S25.

On the other hand, when the link state that allows communication is established in step S21, the 3G-SDI processing block 73a turns on the operation of the wireless communication by the wireless communication device 72 (or maintains the ON state) as shown in step S26. As shown in next step S27, the wireless communication device 72 receives the ancillary data Da wirelessly transmitted from the wireless communication device 64.

As shown in step S28, the wireless video receiver 71 receives the double-speed 3D/2D video signal wirelessly transmitted by the wireless video transmitter 63. As shown in next step S29, the 3G-SDI processing block 73a generates a 3G-SDI signal by adding the ancillary data Da to the head part of the double-speed 3D/2D video signal based on the received double-speed 3D/2D video signal and ancillary data Da. As shown in next step S30, the 3G-SDI processing block 73a forwards the generated 3G-SDI signal to the 3D monitor 11B through the coaxial cable 74.

Figure 12:
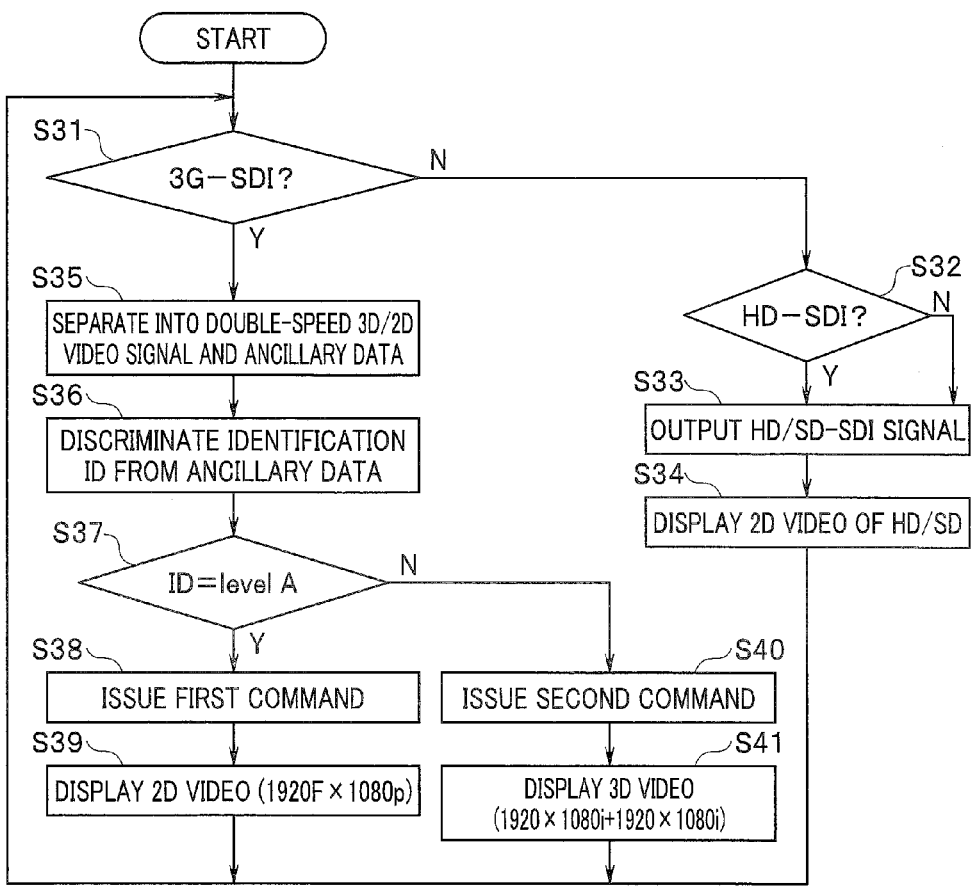
FIG. 12 is a flowchart showing operation of the 3D monitor to which the 3G-SDI signal is inputted.

FIG. 12 shows operation of the 3D monitor 11B to which a video signal, such as a 3G-SDI signal, generated by the wireless reception section 14 is inputted.

As shown in step S31, when the video signal is inputted, a reception SMPTE processing block 51b1 of the video input IF 51b judges whether the inputted video signal is a 3G-SDI signal based on, for example, the clock frequency. When a discrimination result indicates that the video signal is not the 3G-SDI signal, the reception SMPTE processing block 51b1 discriminates whether the video signal is an HD-SDI signal or an SD-SDI signal as shown in next step S32.

As shown in step S33, the discriminated video signal of the HD-SDI signal or the SD-SDI signal is forwarded (outputted) to the video processing section 55b. As shown in step S34, the video processing section 55b executes video signal processing for displaying an HD/SD 2D video on a display section 54b, and the display section 54b displays the HD/SD 2D video.

On the other hand, when it is judged in step S31 that the video signal is a 3G-SDI signal, the reception SMPTE processing block 51b1 separates the 3G-SDI signal into the double-speed 3D/2D video signal and the ancillary data Da as shown in step S35.

In next step S36, an identification ID extraction processing block 51b2 of the reception SMPTE processing block 51b1 extracts the identification ID from the ancillary data Da and discriminates the identification ID. That is, in next step S37, the identification ID extraction processing block 51b2 discriminates whether the identification ID indicates Level A. A discrimination result is then sent to a control section 52b.

When the identification ID indicates Level A in the discrimination result, the control section 52b issues, for example, a first command to control a video processing section 55b to display a double-speed 2D video signal on the display section 54b (controls processing operation of the video processing section 55b) in next step S38. In next step S39, the display section 54b displays the double-speed 2D video signal. In other words, the display section 54b displays the 2D video with an YcrCb signal of 1980×1080p.

When the identification ID indicates Level B instead of Level A in the discrimination result in step S37, the control section 52b issues, for example, a second command to control the video processing section 55b to display a 3D video signal on the display section 54b in step S40. In next step S41, the display section 54b displays a double-speed 3D video signal. In other words, the display section 54b displays the 3D video with an YcrCb signal of 1980×1080i (left eye)+1980×1080i (right eye).

After the processes of steps S34, S39, and S41, the process returns to step S31.

In this way, when the 3G-SDI signal provided with the ancillary information including the identification ID is inputted in the present embodiment, the wireless transmission section 13 wirelessly transmits (transfers) the ancillary data Da as ancillary information including the identification ID, and the wireless reception section 14 discriminates the identification ID from the transferred ancillary data and switches the 3D/2D video of the 3D monitor 11B according to the discriminated identification ID.

Figure 13:
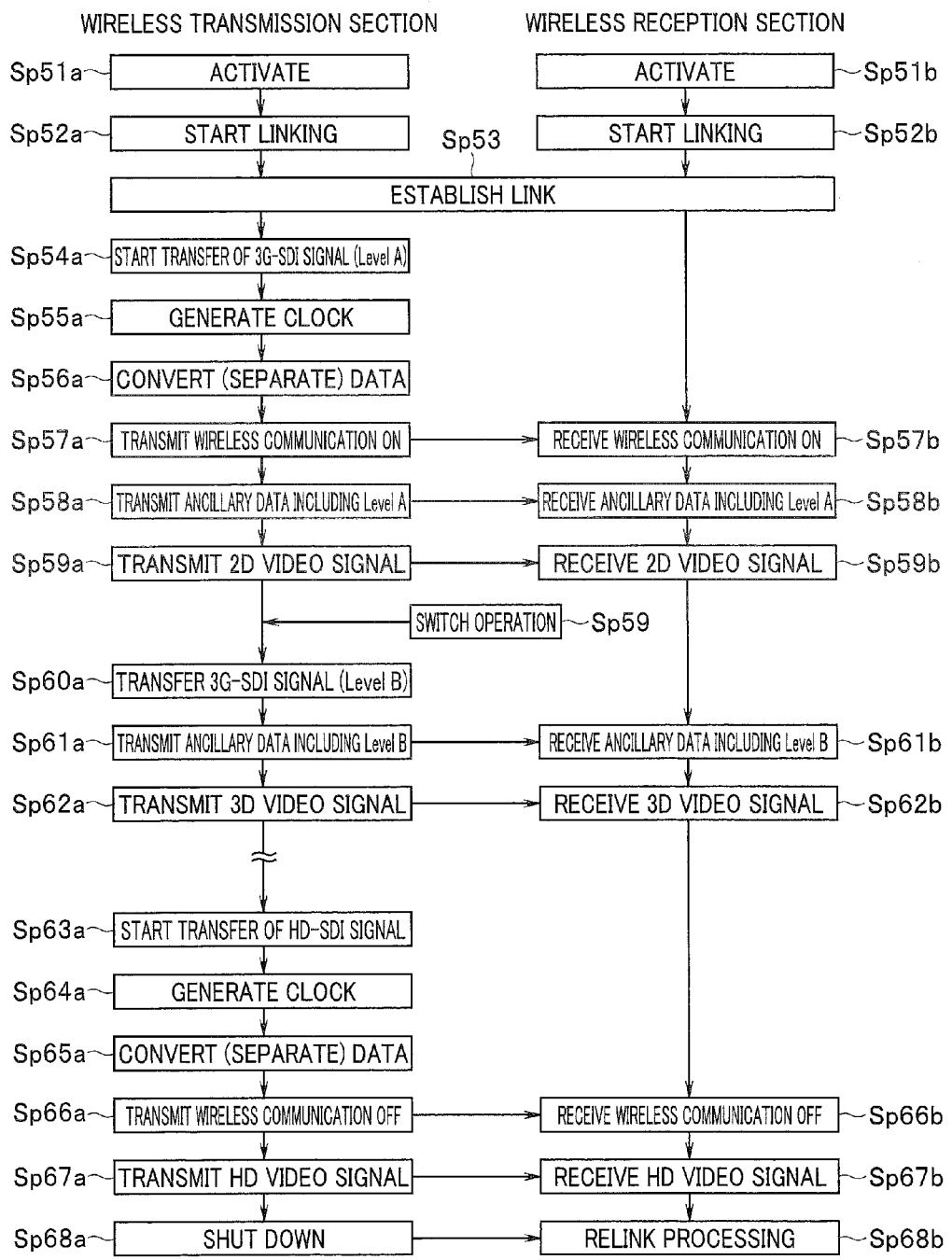
FIG. 13 is a diagram showing processing content in representative operation by the wireless transmission section and the wireless reception section.

FIG. 13 shows operation of transferring the 3D/2D video signal equivalent to the 3G-SDI signal and the identification ID in the ancillary data Da and operation of transferring the HD/SD-SDI signal by the wireless transmission section 13 and the wireless reception section 14 according to the present embodiment. Note that a vertical axis in FIG. 13 indicates a time passage from top to bottom.

The wireless transmission section 13 and the wireless reception section 14 are activated in first processes Sp51a and Sp51b and start operation of linking for checking whether wireless communication can be mutually performed in processes Sp52a and 52b after the activation. In process Sp53 after the start of linking, a link that allows communication is established.

After the establishment of the link, the wireless transmission section 13 starts wireless transfer operation of the double-speed 3D/2D video signal and the ancillary data including the corresponding identification ID based on the 3G-SDI signal (generated by the 3D mixer 9) in process Sp54a. In this case, it is assumed that the identification ID is Level A indicating a 2D video. Note that the identification ID is determined by the 3D mixer 9 as can be understood from the operation described above.

The 3G-SDI processing block 62 of the wireless transmission section 13 generates a clock in process Sp55a and performs data conversion (data separation) in process Sp56a. In process Sp57a, the wireless communication device control section 68 of the wireless transmission section 13 turns on and controls the wireless communication device 64 to perform operation of wireless communication, and the wireless communication device 64 transmits an ON control signal (abbreviated as ON signal in FIG. 13) for ON control (of the wireless communication device 72). The wireless communication device 72 of the wireless reception section 14 receives the ON control signal in process Sp57b, and the wireless communication device 72 maintains the operation state of the wireless communication.

The wireless communication device 64 of the wireless transmission section 13 transmits the ancillary data Da including Level A as the identification ID in process Sp58a, and the wireless video transmitter 63 of the wireless transmission section 13 transmits a double-speed 2D video signal corresponding to Level A in step Sp59a.

The wireless communication device 64 of the wireless reception section 14 receives the ancillary data Da including Level A as the identification ID in process Sp58b, and the wireless video receiver 71 of the wireless reception section 14 receives the double-speed 2D video signal in step Sp59b.

When the operator D1 that performs a surgery wants to perform, for example, a treatment that requires accuracy during the surgery, the operator D1 operates the change-over switch 78 of the polarization glasses 15A in the sterile area Rc to enable the 3D observation. This is indicated by process 59 of switch operation in FIG. 13.

The signal of the operation is received by the wireless receiver 46 of the 3D mixer 9 through the wireless transmitter 79 and is inputted to the instruction signal discrimination section 47. The instruction signal discrimination section 47 discriminates that the signal is a switch instruction signal for the 3D observation and changes the identification ID to Level B.

In response to the change (switch), the wireless transmission section 13 is changed to a state of transferring the double-speed 3D video signal and the ancillary data Da including the identification ID of Level B in process Sp60a.

The wireless communication device 64 of the wireless transmission section 13 transmits the ancillary data Da including Level B as the identification ID in process Sp61a, and the wireless video transmitter 63 of the wireless transmission section 13 transmits a double-speed 3D video signal in step Sp62a.

The wireless communication device 64 of the wireless reception section 14 receives the ancillary data Da including Level B as the identification ID in process Sp61b, and the wireless video receiver 71 of the wireless reception section 14 receives the double-speed 3D video signal in step Sp62b. In this case, the wireless reception section 14 outputs a 3G-SDI signal equivalent to the high-definition 3D video to the 3D monitor 11B, and the 3D monitor 11B displays the high-definition 3D video.

The operator D1 can smoothly perform the treatment that requires accuracy based on the high-definition 3D video.

Note that FIG. 13 further shows a state in which the HD-SDI signal can be transferred. It is assumed that a state of transferring the HD-SDI signal is set in process Sp63a.

The 3G-SDI processing block 62 of the wireless transmission section 13 generates a clock with a shaped waveform from the HD-SDI signal in next process Sp64a and performs data conversion (data separation) in process Sp65a. In process Sp66a, the wireless communication device control section 68 of the wireless transmission section 13 applies OFF control for not performing operation of wireless communication to the wireless communication device 64, and the wireless communication device 64 transmits an OFF control signal. The wireless communication device 72 of the wireless reception section 14 receives the OFF control signal in process Sp66b. The wireless communication device 72 enters an OFF state in which the operation of the wireless communication is not performed.

In process Sp67a, the wireless video transmitter 63 of the wireless transmission section 13 transmits an HD video signal. In response to the transmission, the wireless video receiver 71 of the wireless reception section 14 receives the HD video signal in process Sp67b.

The wireless transmission section 13 is shut down in process Sp68a, and the wireless reception section 14 executes relink processing or the like in process Sp68b.

According to the present embodiment that operates in this way, a wireless video transmitter/receiver configured to wirelessly transmit and receive a high-definition 2D video signal or a high-definition 3D video signal provided with ancillary information including identification information and a wireless ancillary information transmitter/receiver configured to wirelessly transmit and receive the ancillary information including the identification information can be used to easily construct a wireless transfer system, and a wireless transfer system also corresponding to transmission and reception of a 2D video signal not provided with the identification information can be easily constructed.

According to the present embodiment, a wireless transfer system compliant with a signal transfer standard of 3G-SDI as a high video signal transfer standard can be easily constructed. That is, a wireless transfer system corresponding to a wireless video transmitter/receiver configured to wirelessly transmit and receive a high-definition 2D video signal or a high-definition 3D video signal provided with ancillary information including the identification information in the 3G-SDI signal and also corresponding to transmission and reception of a 2D video signal not provided with the identification information compliant with a signal standard with a lower signal transfer rate can be easily constructed.

In the present embodiment, when a 2D video signal not provided with the identification information is to be transmitted and received, the operation of wireless communication between the wireless communication device 64 and the wireless communication device 72 included in the wireless ancillary information transmitter/receiver can be stopped to set power saving.

According to the present embodiment, when the operator D1 or D2 (as a user of endoscope) that uses the 3D endoscope 5 to perform a medical action, such as a surgery, by using the 3D endoscope 5 in the sterile area Rc desires to switch the 3D observation and the 2D observation, the identification information of the 3D/2D video generated by the 3D mixer 9 arranged in the non-sterile area Rn can be changed from the sterile area Rc (without involvement of a nurse in the non-sterile area Rn), and the operability can be improved.

In the description above, the wireless transmission section 13 extracts the ancillary data Da including the identification ID added to the head part of the double-speed 3D/2D video signal from the 3G-SDI signal inputted from the 3D mixer 9, and the wireless communication device 64 included in the wireless ancillary information transmission section wirelessly transmits the extracted ancillary data Da.

Figure 14:
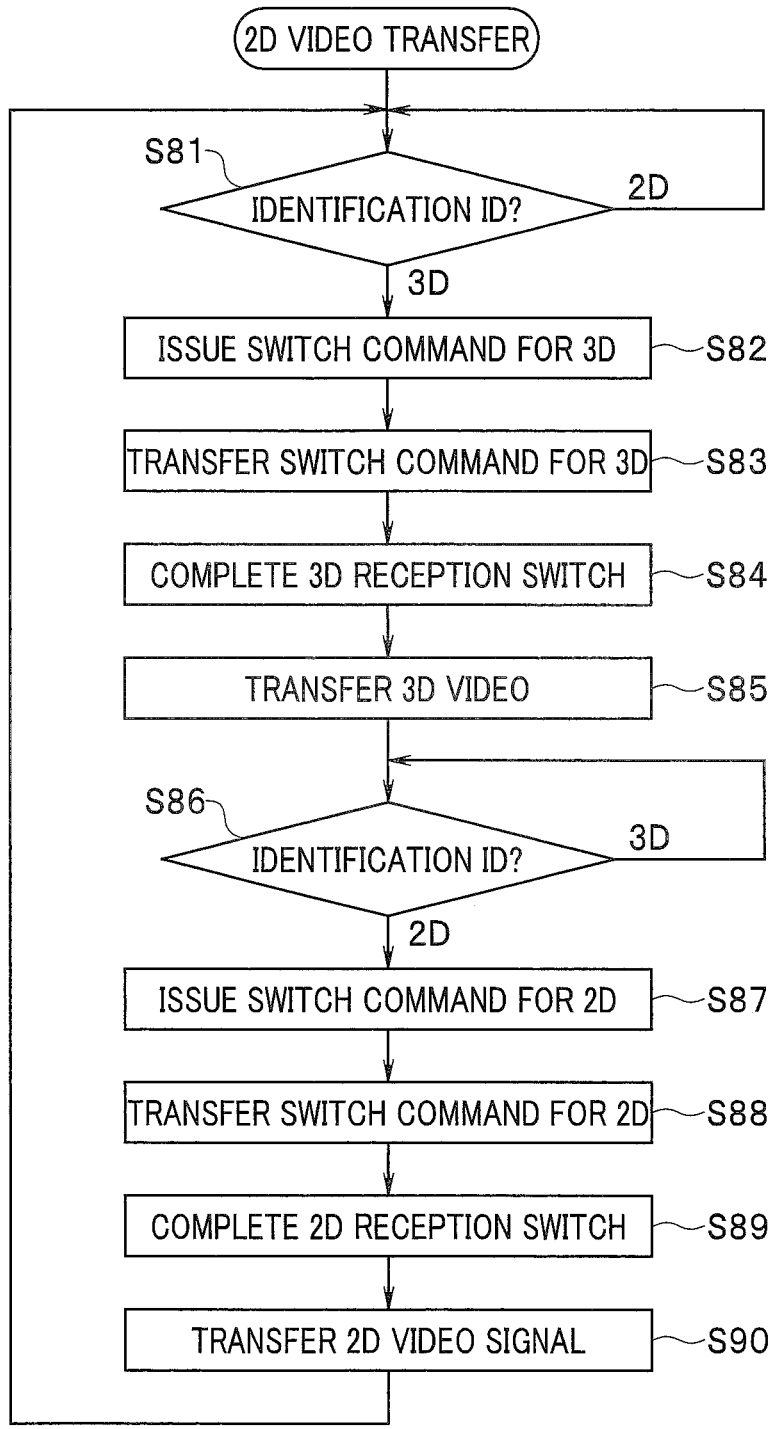
FIG. 14 is a flowchart showing operation of transferring a command according to the identification ID of a 3D/2D video signal in the 3G-SDI signal.

In contrast, as shown in following FIG. 14, the wireless transmission section 13 may convert the identification ID to a command for distinguishing and displaying the double-speed 3D/2D video signal and insert the command into the identification ID part in the ancillary data Da. The wireless reception section 14 may also perform corresponding operation. Note that the 3D video or the 2D video will be simply abbreviated as 3D or 2D.

It is assumed that in the initial state, the wireless transmission section 13 is in a state of transmitting 2D. Consequently, the wireless transmission section 13 (3G-SDI processing block 62 of the wireless transmission section 13) judges whether the identification ID transmitted by the wireless communication section 64 is an identification ID of 2D in step S81. When the identification ID is an identification ID of 2D, the process returns to step S81.

When the identification ID is an identification ID of 3D, the wireless transmission section 13 (3G-SDI processing block 62 of the wireless transmission section 13) issues a command corresponding to the identification ID of 3D for switching 2D to 3D in step S82. In next step S83, the wireless communication device 64 of the wireless transmission section 13 wirelessly transfers a command corresponding to the identification ID of 3D. In next step S84, the wireless reception section 14 receives the command corresponding to the identification ID of 3D, and the state of receiving the video signal of 3D, that is, the reception switch is completed.

In next step S85, the wireless transmission section 13 transfers the video signal of 3D.

In next step S86, the wireless transmission section 13 discriminates the identification ID, and when the identification ID indicates 3D, a process of step S86 is continued. When the identification ID indicates 2D (switched from 3D), the wireless transmission section 13 (3G-SDI processing block 62 of the wireless transmission section 13) issues a command corresponding to the identification ID of 2D for switching 3D to 2D in next step S87. In next step S88, the wireless communication device 64 of the wireless transmission section 13 wirelessly transfers a command corresponding to the identification ID of 2D. In next step S89, the wireless reception section 14 receives the command corresponding to the identification ID of 2D, and the state of receiving the video signal of 2D, that is, the reception switch of 2D is completed.

In next step S90, the wireless transmission section 13 transfers the video signal of 2D, and the process returns to step S81.

Note that in the embodiment described above, the 3D/2D instruction operation means (or 3D/2D instruction operation portion) for switching the identification information generated by the 3D mixer 9 from the sterile area Rc may be formed by a 3D/2D change-over switch provided on the grasping portion 23 of the 3D endoscope 5.

What is claimed is:

1. A wireless transfer system comprising:
  a wireless transmission section comprising:
    an input section configured to receive one of a first video signal and a second video signal as an input signal, the first video signal being compliant with a first signal transfer standard provided with, at a head part of a high-definition video signal, ancillary information including at least identification information indicating one of a high-definition 3D video signal and a high-definition 2D video signal, the second video signal having a signal transfer rate lower than the first video signal and being compliant with a second signal transfer standard not including the identification information;
    a video signal extraction section configured to extract one of the high-definition video signal and the second video signal from the input signal;
    an ancillary information extraction section configured to extract the ancillary information including at least the identification information from the input signal;
    a wireless video transmitter configured to wirelessly transmit one of the high-definition video signal and the second video signal extracted by the video signal extraction section;
    a wireless ancillary information transmitter configured to wirelessly transmit the ancillary information extracted by the ancillary information extraction section, separately from one of the high-definition video signal and the second video signal wirelessly transmitted by the wireless video transmitter; and
    a control section configured to control operation of the wireless ancillary information transmitter according to an extraction result of the ancillary information; and
  a wireless reception section comprising:
    a wireless video receiver configured to receive one of the high-definition video signal and the second video signal wirelessly transmitted from the wireless video transmitter;
    a wireless ancillary information receiver configured to receive the ancillary information wirelessly transmitted from the wireless ancillary information transmitter; and
    an output signal control section configured to add the ancillary information to the high-definition video signal and output the high-definition video signal when the ancillary information is received and configured to output the second video signal when the ancillary information is not received, according to a reception result of the wireless video receiver and a reception result of the wireless ancillary information receiver.

2. The wireless transfer system according to claim 1, wherein
  the wireless ancillary information transmitter wirelessly transmits the ancillary information extracted by the ancillary information extraction section in a band different from a band for one of the high-definition video signal and the second video signal wirelessly transmitted by the wireless video transmitter.

3. The wireless transfer system according to claim 1, wherein
  one of the high-definition 3D video signal and the high-definition 2D video signal forming the first video signal provided with the ancillary information including the identification information is a video signal of a 3G-SDI standard capable of transferring 3 gigabits/second, and
  the control section controls the wireless ancillary information transmitter to perform wireless transmission when the ancillary information extraction section extracts the ancillary information and controls the wireless ancillary information transmitter to stop transmission operation of performing wireless transmission when the ancillary information extraction section does not extract the ancillary information.

4. The wireless transfer system according to claim 3, further comprising:
  a stereoscopic endoscope provided with a pair of two image pickup sections on left and right; two video signal generation sections configured to generate left and right 2D video signals from left and right image pickup signals picked up by the two image pickup sections; and a 3D mixer configured to generate one of the high-definition 3D video signal of the 3G-SDI standard and the high-definition 2D video signal of the 3G-SDI standard provided with the ancillary information including the identification information from the left and right 2D video signals generated by the two video signal generation sections according to instruction operation of a user for generating one of a 3D video and a 2D video, wherein
  the 3D mixer outputs the generated video signal of the 3G-SDI standard to the input section.

5. The wireless transfer system according to claim 4, further comprising:
  an instruction operation switch for the user performing a medical action by using the stereoscopic endoscope to perform the instruction operation for generating one of the 3D video and the 2D video from a sterile area in which a sterilization process is applied; and a 3D/2D instruction signal transmission section configured to wirelessly transmit an instruction signal based on the instruction operation to the 3D mixer arranged in a non-sterile area in which the sterilization process is not applied.

6. The wireless transfer system according to claim 4, wherein
  the 3D mixer comprises: a wireless receiver configured to wirelessly receive the instruction signal of the instruction operation by the user for generating one of the 3D video and the 2D video; and a discrimination circuit configured to discriminate which one of the 3D video and the 2D video is indicated by the instruction signal received by the wireless receiver based on the instruction operation for generating one of the 3D video and the 2D video.

7. The wireless transfer system according to claim 6, further comprising:
  a first 3D monitor capable of displaying one of a high-definition 3D video with 1920×1080 pixels and a high-definition 2D video with 1920×1080 pixels by receiving, through a wire, one of the high-definition 3D video signal of the 3G-SDI standard and the high-definition 2D video signal of the 3G-SDI standard provided with the ancillary information forming the first video signal outputted from the 3D mixer; and a second 3D monitor configured to receive, through a wire, one of the first video signal of the 3G-SDI standard, in which the ancillary information is added to the high-definition video signal outputted from the wireless video receiver, and the second video signal of an HD-SDI standard.

8. The wireless transfer system according to claim 7, further comprising two 3D glasses on the first 3D monitor and the second 3D monitor for observing the high-definition 3D video, wherein the two 3D glasses comprise: an instruction operation switch for performing instruction operation for generating one of the 3D video and the 2D video from a sterile area subjected to a sterilization process, by a user that performs a medical action by using the stereoscopic endoscope; and a wireless transmitter forming a 3D/2D instruction signal transmission section configured to wirelessly transmit an instruction signal based on the instruction operation to the 3D mixer arranged in a non-sterile area not subjected to the sterilization process.

9. The wireless transfer system according to claim 8, wherein each of the wireless ancillary information transmitter and the wireless ancillary information receiver is formed by a wireless communication device configured to perform two-way communication.

10. The wireless transfer system according to claim 5, wherein the 3D mixer comprises: a wireless receiver configured to receive the instruction signal wirelessly transmitted by the 3D/2D instruction signal transmission section; and a discrimination circuit configured to discriminate which one of the 3D video and the 2D video is indicated by the instruction signal received by the wireless receiver based on the instruction operation for generating one of the 3D video and the 2D video.

11. The wireless transfer system according to claim 4, further comprising:

a first 3D monitor capable of displaying one of a high-definition 3D video with 1920×1080 pixels and a high-definition 2D video with 1920×1080 pixels by receiving, through a wire, one of the high-definition 3D video signal of the 3G-SDI standard and the high-definition 2D video signal of the 3G-SDI standard provided with the ancillary information forming the first video signal outputted from the 3D mixer; and a second 3D monitor configured to receive, through a wire, one of the first video signal of the 3G-SDI standard, in which the ancillary information is added to the high-definition video signal outputted from the wireless video receiver, and the second video signal of an HD-SDI standard.

12. The wireless transfer system according to claim 1, further comprising:

a stereoscopic endoscope provided with a pair of two image pickup sections on left and right; two video signal generation sections configured to generate left and right 2D video signals from left and right image pickup signals picked up by the two image pickup sections; and a 3D mixer configured to generate one of the high-definition 3D video signal and the high-definition 2D video signal provided with the ancillary information including the identification information from the left and right 2D video signals generated by the two video signal generation sections according to instruction operation of a user for generating one of a 3D video and a 2D video, wherein the 3D mixer outputs generated one of the high-definition 3D video signal and the high-definition 2D video signal to the input section.

13. The wireless transfer system according to claim 12, further comprising:

an instruction operation switch for the user performing a medical action by using the stereoscopic endoscope to perform the instruction operation for generating one of the 3D video and the 2D video from a sterile area in which a sterilization process is applied; and a 3D/2D instruction signal transmission section configured to wirelessly transmit an instruction signal based on the instruction operation to the 3D mixer arranged in a non-sterile area in which the sterilization process is not applied.

* * * * *